US00PP13339P2

(12) United States Plant Patent
Oliver

(10) Patent No.: US PP13,339 P2
(45) Date of Patent: Dec. 10, 2002

(54) HEUCHERA PLANT NAMED 'SILVER LODE'

(76) Inventor: Charles Oliver, 921 Scottdale-Dawson Rd., Scottdale, PA (US) 15683

( * ) Notice: Subject to any disclaimer, the term of this patent is extended or adjusted under 35 U.S.C. 154(b) by 0 days.

(21) Appl. No.: 09/968,330

(22) Filed: Sep. 30, 2001

(51) Int. Cl.[7] ..... A01H 5/00
(52) U.S. Cl. ..... Plt./263
(58) Field of Search ..... Plt./263

*Primary Examiner*—Bruce R. Campell
*Assistant Examiner*—Annette H. Para
(74) *Attorney, Agent, or Firm*—C. A. Whealy

(57) ABSTRACT

A distinct cultivar of Heuchera plant named 'Silver Lode', characterized by its uniformly mounded plant habit; upper leaf surfaces gray green in color with contrasting darker gray green venation; lower leaf surfaces dark red purple in color; numerous showy white flowers arranged on erect panicles; tight cylindrical panicle arrangement; and excellent garden performance.

2 Drawing Sheets

BOTANICAL CLASSIFICATION

*Heuchera sp.*

VARIETY DENOMINATION

'Silver Lode'.

BACKGROUND OF THE INVENTION

The present invention relates to a new and distinct cultivar of Heuchera plant, botanically known as *Heuchera sp.* and hereinafter referred to by the name 'Silver Lode'.

The new Heuchera is a product of a planned breeding program conducted by the Inventor in Scottdale, Pa. The objective of the breeding program is to create new Heuchera cultivars having good plant vigor, dense and uniform plant habit, and showy and attractive flower and leaf coloration.

The new Heuchera was discovered by the Inventor in a controlled environment in Scottdale, Pa., from seedling progeny from a cross-pollination made by the Inventor in May, 1996, of the Heuchera cultivar Petite Bronze Pearl, not patented, as the female, or seed, parent with the Heuchera cultivar Harmonic Convergence, disclosed in U.S. Plant Pat. No. 11,111, as the male, or pollen, parent. The new Heuchera was selected by the Inventor in May, 1997. The selection of this plant was based on its desirable flower and foliage coloration.

Asexual reproduction of the new Heuchera by cuttings taken in a controlled environment in Scottdale, Pa., since August, 1997, has shown that the unique features of this new Heuchera are stable and reproduced true to type in successive generations.

SUMMARY OF THE INVENTION

The cultivar Silver Lode has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Silver Lode'. These characteristics in combination distinguish 'Silver Lode' as a new and distinct cultivar:

1. Full and densely foliated; uniformly mounded plant habit.
2. Upper leaf surfaces gray green in color with contrasting darker gray green venation; lower leaf surfaces dark red purple in color.
3. Numerous showy white flowers arranged on erect panicles.
4. Tight cylindrical panicle arrangement.
5. Excellent garden performance.

Plants of the new Heuchera differ from plants of the female parent, the cultivar Petite Bronze Pearl, in side-by-side comparisons conducted by the Inventor in Scottdale, Pa. in the following characteristics:

1. Upper leaf surfaces of plants of the new Heuchera are gray green in color whereas upper leaf surfaces of plants of the cultivar Petite Bronze Pearl are bronze in color.
2. Leaves of plants of the new Heuchera are larger than leaves of plants of the cultivar Petite Bronze Pearl.
3. Plants of the new Heuchara have taller panicles than plants of the cultivar Petite Bronze Pearl.
4. Sepal color of plants of the new Heuchera is white whereas sepal color of plants of the cultivar Petite Bronze Pearl is light pink.

Plants of the new Heuchera differ from plants of the male parent, the cultivar Harmonic Convergence, in side-by-side comparisons conducted by the Inventor in Scottdale, Pa. in the following characteristics:

1. Upper leaf surfaces of plants of the new Heuchera are more gray green in color than upper leaf surfaces of plants of the cultivar Harmonic Convergence.
2. Panicles of plants of the new Heuchera are upright whereas panicles of plants of the cultivar Harmonic Convergence are upright to outwardly spreading.
3. Panicles of plants of the new Heuchera are not basally branching whereas panicles of plants of the cultivar Harmonic Convergence are basally branching.
4. Sepal color of plants of the new Heuchera is white whereas sepal color of plants of the cultivar Harmonic Convergence is pink.

5. Petals of plants of the new Heuchera are not recurved whereas petals of plants of the cultivar Harmonic Convergence are recurved.

Compared to plants of the sibling cultivar Raspberry Ice, U.S. Plant Patent application filed concurrently with this application, plants of the new Heuchera have more upright panicles, develop more panicles per plant during the flowering season and also differ in flower color as plants of the cultivar Raspberry Ice have pink-colored flowers.

Plants of the new Heuchera can be compared to plants of the cultivar Silver Scrolls, disclosed in U.S. Plant Pat. No. 12,066. In side-by-side comparisons conducted by the Inventor in Scottdale, Pa., plants of the new Heuchera differed from plants of the cultivar Silver Scrolls in the following characteristics:

1. Plants of the new Heuchera have taller panicles than plants of the cultivar Silver Scrolls.
2. Upper leaf surfaces of plants of the new Heuchera do not have a metallic sheen whereas upper leaf surfaces of the cultivar Silver Scrolls have a metallic sheen.

Plants of the new Heuchera can also be compared to plants of the cultivar Pewter Veil, disclosed in U.S. Plant Pat. No. 8,984. In side-by-side comparisons conducted by the Inventor in Scottdale, Pa., plants of the new Heuchera differed from plants of the cultivar Pewter Veil in the following characteristics:

1. Upper leaf sufaces of plants of the new Heuchera are gray green in color with contrasting darker gray green venation whereas upper leaf surfaces of plants of the cultivar Pewter Veil are gray green suffused with purple coloration.
2. Panicles of plants of the new Heuchera are erect whereas panicles of plants of the cultivar Pewter Veil are outwardly spreading.
3. Plants of the new Heuchera have showy white-colored flowers whereas plants of the cultivar Pewter Veil have non-showy yellow green-colored flowers.

BRIEF DESCRIPTION OF THE PHOTOGRAPHS

The accompanying colored photographs illustrate the overall appearance of the new Heuchera, showing the colors as true as it is reasonably possible to obtain in colored reproductions of this type. Colors in the photographs may differ slightly from the color values cited in the detailed botanical description which accurately describe the colors of the new Heuchera.

The photograph on the first sheet comprises a side perspective view of a typical flowering plant of 'Silver Lode'.

The photograph on the second sheet comprises a close-up view of typical leaves of 'Silver Lode'.

DETAILED BOTANICAL DESCRIPTION

In the following description, color references are made to The Royal Horticultural Society Colour Chart except where general terms of ordinary dictionary significance are used. The following observations and measurements describe pinched plants grown in Keller, Tex. during the summer and fall outdoors under full sun and cultural conditions which approximate commercial practice. Plants used for the photographs and descriptions were grown as single plants in one-gallon containers and were about one year old. Measurements and numerical values represent averages taken from a group of flowering plants.

Botanical classification: *Heuchera sp.* cultivar Silver Lode.

Parentage:

*Female, or seed, parent.*—*Heuchera sp.* cultivar Petite Bronze Pearl, not patented.

*Male, or pollen, parent.*—*Heuchera sp.* cultivar Harmonic Convergence, disclosed in U.S. Plant Pat. No. 11,111.

Propagation:

*Type.*—By cuttings.

*Time to initiate roots.*—About 14 days at 23° C.

*Time to produce a rooted cutting.*—About 30 days at 23° C.

*Root description.*—Fine, fibrous and well-branched.

Plant description:

*Appearance.*—Perennial; basal rosette plant habit with leaves developing from the base; densely foliated; full, mounded and uniform plant habit with upright panicles with showy white-colored flowers. Vigorous and robust growth habit.

*Plant size.*—Height: Soil level to top of foliar plane: About 16 cm. Soil level to top of panicles: About 55 cm. Diameter or spread: About 53 cm.

*Foliage description.*—Arrangement: Basal rosette, single. Length: About 9.3 cm. Width: About 9.2 cm. Shape: Roughly ovate to cordate. Apex: Mostly rounded. Base: Cordate. Margin: Crenate and serrulate with fine ciliation. Texture: Upper surface, smooth; lower surface with sparse pubescence. Venation pattern: Palmate, reticulate. Color: Young and mature foliage, upper surface: Darker gray green than 198A. Young and mature foliage, lower surface: Closest to, but more red purple than between 79A and 79B. Venation, upper and lower surfaces: Much darker gray green than 198A, close to 202A. Petiole: Length: About 14 cm. Diameter: About 3 mm. Texture, upper and lower surfaces: Sparsely pubescent. Color, upper and lower surfaces: Close to, but more dull than 187A.

Flower description:

*Appearance/arrangement.*—Single campanulate flowers arranged on numerous erect panicles; panicles, tight cylindrical arrangement with more than 90 flowers and flower buds per flowering stem with 4 to 5 flowers per lateral pedicel. Flowers face outward. Flowering continuous with at least 18 flowering stems per plant developing throughout the flowering period. Flowers not persistent. Flowers not fragrant.

*Time of flowering.*—Under natural conditions, plant flower in the late spring.

*Inflorescence longevity.*—Individual inflorescences last about one week on the plant.

*Inflorescence size.*—Length: About 33 cm. Diameter: About 3.5 cm.

*Flower size.*—Diameter: About 5 mm. Depth (height): About 6 mm.

*Flower buds.*—Height: About 2.5 mm. Diameter: About 2 mm. Shape: Spherical to ovoid. Color, at stage of showing color: 187A.

*Sepals.*—Quantity/arrangement: Five sepals; radially symmetrical and fused at base. Length: About 5 mm. Width: About 2 mm. Shape: Elongate. Apex: Acute. Margin: Entire. Texture: Pubescent. Color: When opening, upper and lower surfaces: 187A. Fully opened, upper surface: White, close to 155D; towards the apex slightly tinged with tiny red purple, close to 187A, spots. Fully opened, lower surface: White, close to 155D.

*Petals.*—Quantity/arrangement: Five minute petals; radially symmetrical and fused at base. Length: About 4.5 mm. Width: About 1 mm. Shape: Narrowly spatulate. Apex: Acute. Margin: Entire. Texture: Smooth. Color: When opening and fully opened, upper and lower surfaces: 155D.

*Bracts.*—Quantity/arrangement: One at base of flower; leaf-like. Length: About 5.5 mm. Width: About 3 mm. Shape: Roughly ovate. Apex: Mucronate. Base: Attenuate, sessile. Margin: Deeply serrate with ciliation. Texture: Smooth. Color, upper and lower surfaces: Close to 187A.

*Peduncle.*—Strength: Strong; flexible. Aspect: Erect. Length: About 53 cm. Diameter: About 3.5 mm. Texture: Smooth. Color: Mostly green, close to 148A with some anthocyanin, close to 59A.

*Pedicels.*—Strength: Strong; wiry. Aspect: About 45 to 50° from vertical. Length: About 1.6 cm. Diameter: Less than 1 mm. Texture: Smooth. Color: Close to 146A.

*Reproductive organs.*—Androecium: Stamen number: Five per flower. Anther shape: Bi-lobed. Anther length: Less than 1 mm. Anther color: Close to 33A. Amount of pollen: None observed. Gynoecium: Pistil number: One per flower. Pistil length: About 3.5 mm. Stigma shape: Forked, linear. Stigma color: Close to 155D. Style color: Close to 155D. Ovary color: Close to 155D.

*Seed/fruit.*—Seed/fruit production has not been observed.

Disease/pest resistance: Resistance to pathogens and pests common to Heuchera has not been observed on plants grown under commercial conditions.

Temperature tolerance: Plants of the new Heuchera have demonstrated good tolerance to night temperatures as low as −35° C. and day temperatures as high as 45° C.

It is claimed:

1. A new and distinct cultivar of Heuchera plant named 'Silver Lode', as illustrated and described.

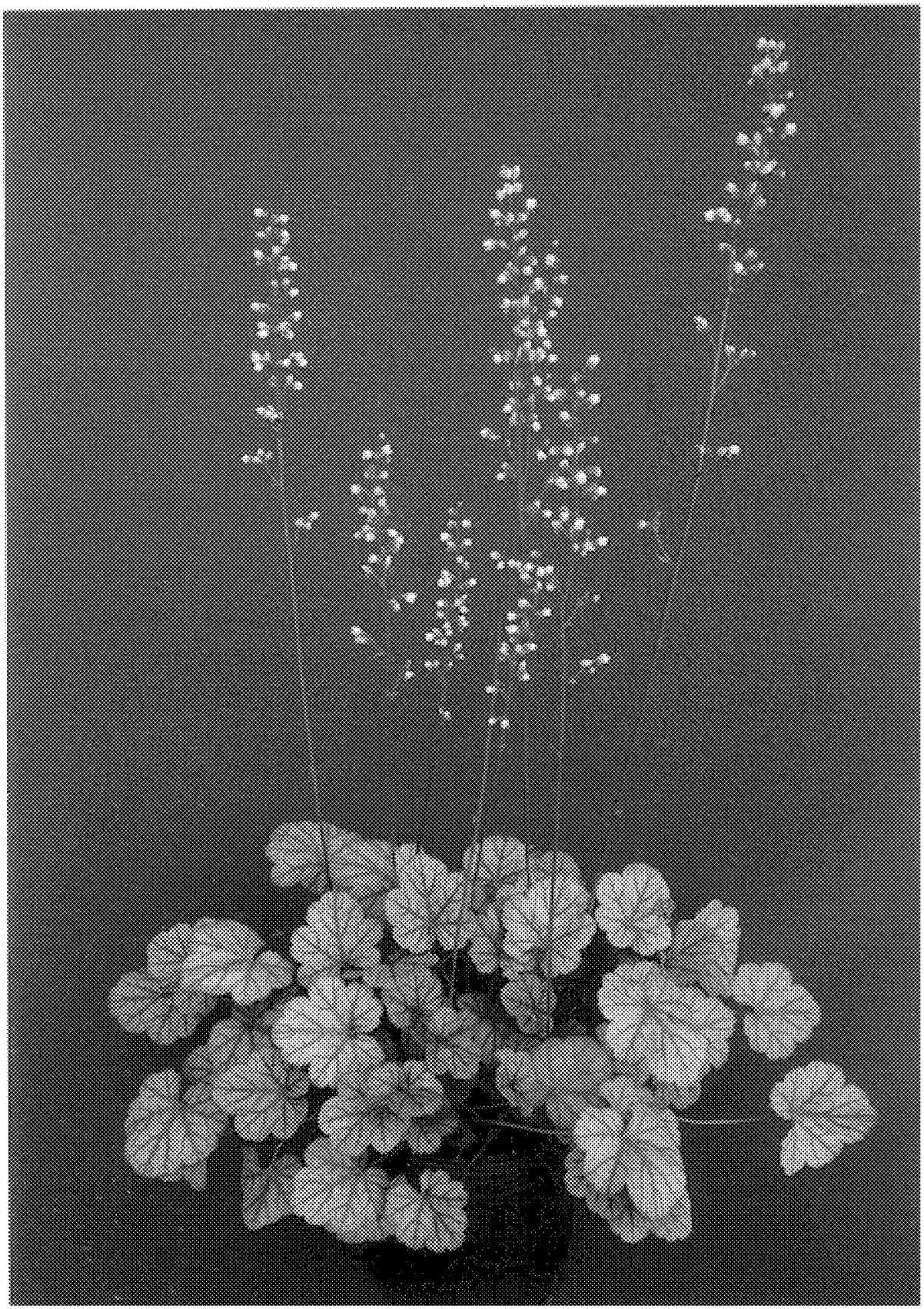

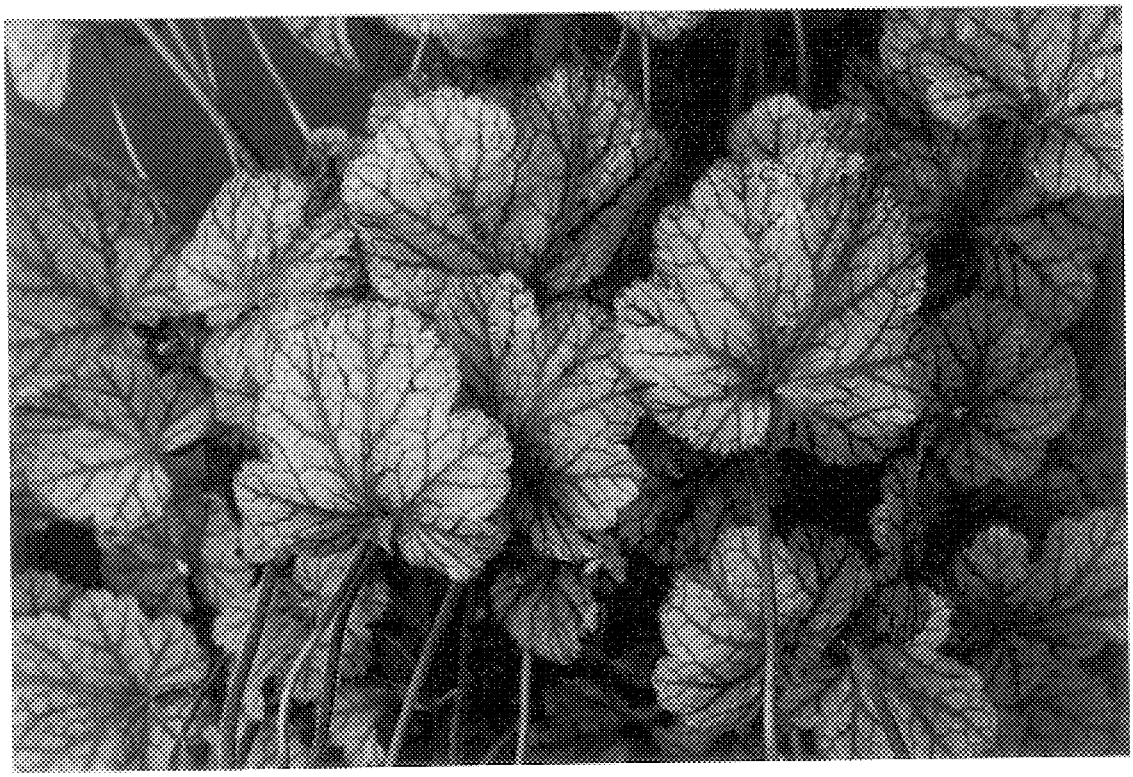

* * * * *